United States Patent
Stange et al.

(10) Patent No.: US 7,361,697 B2
(45) Date of Patent: Apr. 22, 2008

(54) PROSTHESIS MATERIAL

(75) Inventors: Frank Stange, Usingen (DE); Novica Savic, Wehrheim (DE); Albert Erdrich, Nauheim (DE); Teresa Puchalska, Neu-Anspach (DE); Bettina Korthaus, Schmitten (DE)

(73) Assignee: Heraeus Kulzer GmbH & Co.KG, Hanau (DE)

( * ) Notice: Subject to any disclaimer, the term of this patent is extended or adjusted under 35 U.S.C. 154(b) by 538 days.

(21) Appl. No.: 11/046,933

(22) Filed: Jan. 31, 2005

(65) Prior Publication Data

US 2005/0131098 A1 Jun. 16, 2005

Related U.S. Application Data

(62) Division of application No. 10/103,205, filed on Mar. 21, 2002, now Pat. No. 6,881,360.

(30) Foreign Application Priority Data

Mar. 22, 2001 (DE) ................................ 101 14 243

(51) Int. Cl.
A61K 6/083 (2006.01)
A61C 5/00 (2006.01)
A61F 2/50 (2006.01)

(52) U.S. Cl. ........................ 523/115; 523/116; 523/117; 433/228.1

(58) Field of Classification Search ................ 523/115, 523/116
See application file for complete search history.

(56) References Cited

U.S. PATENT DOCUMENTS

| 2,358,730 A | 9/1944 | Nelson et al. |
| 2,423,330 A | 7/1947 | Levine |
| 2,491,147 A | 12/1949 | Zahn |
| 3,083,459 A | 4/1963 | McMurray et al. |
| 4,281,991 A | 8/1981 | Michl et al. ................ 433/202 |
| 4,583,947 A | 4/1986 | Hazar ........................ 433/171 |
| 4,681,543 A | 7/1987 | Monroy ..................... 433/196 |
| 4,746,469 A | 5/1988 | Yamashita .................. 264/18 |
| 4,940,676 A | 7/1990 | Evans ........................ 501/16 |
| 4,983,334 A | 1/1991 | Adell ......................... 264/16 |
| 5,430,074 A | 7/1995 | Barnes et al. .............. 523/115 |
| 5,449,703 A | 9/1995 | Mitra et al. ................. 522/57 |
| 5,684,103 A | 11/1997 | Jia et al. ................... 526/218.1 |
| 5,708,051 A | 1/1998 | Erdrich et al. ............. 523/116 |
| 5,969,000 A | 10/1999 | Yang et al. ................ 523/116 |
| 6,077,075 A | 6/2000 | Bedard et al. ............. 433/167 |
| 6,426,373 B1 | 7/2002 | Stange et al. ............. 523/116 |
| 6,660,194 B1 | 12/2003 | Arita ......................... 264/17 |
| 2003/0113689 A1 | 6/2003 | Sun et al. .................. 433/167 |

FOREIGN PATENT DOCUMENTS

| DE | 363 9067 A1 | 5/1987 |
| DE | 195 02 751 A1 | 8/1996 |
| DE | 198 48 886 C2 | 5/2000 |

*Primary Examiner*—Tae H Yoon
(74) *Attorney, Agent, or Firm*—Norris McLaughlin & Marcus PA

(57) ABSTRACT

Prosthesis material having improved stability during storage, reduced plaque affinity and improved polishing properties.

1 Claim, No Drawings

PROSTHESIS MATERIAL

This application is a Division of application Ser. No. 10/103,205 filed 21 Mar. 2002, now U.S. Pat. No. 6,881,360.

The invention relates to a process for producing a prosthesis, a prosthesis material and its applications.

In general, three principally different material classes are known in the art for carrying out total prosthetic work. They are: two-component materials based on polymethyl methacrylate (PMMA), PMMA-free thermal-hardening materials as well as injection molding masses suitable for thermoplastic processing.

What all these materials have in common is the work that is necessary with regard to the preparations for plastics processing.

After taking a precision impression on the patient and creating a working model made of plaster, a so-called base plate is applied and polymerized on the plaster model by means of a hardenable material. This base plate is the foundation for the setting up of the prosthesis in wax, which follows later, and provides sufficient stability even for brief try-ons in the patient's mouth.

However, it is disadvantageous that, before the conversion of the wax impression into plastic, this base plate must be removed and replaced with wax that is to be boiled out.

In another step, the work mounted in wax is completely embedded in plaster and, following the hardening of the plaster, the wax is removed by way of heating. The plastic is then introduced and solidified in accordance with various methods inside the hollow space achieved in this manner.

The following aspects of these traditional processes are disadvantageous:
- the complete embedding with the use of plaster is time-consuming because of the necessary setting time,
- due to the incompatibility of the plaster, which contains water, and the plastic, it is necessary to use an insulation agent, which repeatedly causes discolorations of the plastic due to insufficient insulation,
- the use of light-hardening materials is precluded and any control during the filling process is not possible.

It is particularly disadvantageous that all plastic must always be introduced and polymerized in one step, which has a negative effect on the form stability due to polymerization shrinkage and thermal shrinkage.

Based on the above, there results the objective to provide, in particular a process for producing a prosthesis and a related prosthesis material that no longer have, at least in part, the above-mentioned disadvantages. This applies especially with regard to the form stability, which is awaiting improvement.

According to the invention, this objective is achieved with a process, a prosthesis material and with the applications.

According to the invention, first, an anatomic impression of the jaw of a patient is taken using a conventional impression mass, for example, addition cross-linking silicone or alginate.

After this, a working model, consisting in particular of plaster, is constructed. A base plate of a hardenable prosthesis material, especially of a material in accordance with the invention (see below), is then applied and subsequently hardened. This constitutes the core of present invention, i.e. the use of a prosthesis material, in particular a material in according to the invention, as base plate material.

An insulating film is now applied to the base plate in order to subsequently obtain a teeth impression in wax on the insulated base plate. The teeth arches are held from the outside using an investment material, for example, a transparent addition cross-linking silicone or light-hardening embedding material on methacrylate basis. Afterwards, the wax impression is boiled out and the insulating film is removed in order to now fill the hollow space resulting from the boiling out of the wax with the prosthesis material and to subsequently harden the prosthesis material.

In another variant of the process according to the invention, first, a precision impression is taken using an impression mass, then a working model is created, a base plate of a light-hardenable prosthesis material is applied and hardened in order to, finally, obtain and harden a tooth arrangement in the light-hardenable prosthesis material.

The following embodiments of the process according to the invention have proven themselves in practical applications and have, therefore, turned out to be advantageous.

First and foremost, it is advantageous if in the last process step of the second variant, the tooth arrangement is created step by step, while taking into consideration the jaw ratios, in particular using an articulator, and hardened point-by-point with light, because only this ensures the correct position with respect to the antagonist teeth; and a displacement due to shrinkage can be avoided by way of point-by-point hardening.

Furthermore, it is also advantageous if, in a final step, the prosthesis as a whole is hardened again using light irradiation following the point-by-point hardening in order to achieve a homogenous polymerization conversion that is needed for obtaining sufficient stabilities.

Also advantageous is the use of a compound for the base plate material that is comprised of the following components:
1. multifunctional urethane methacrylate/-acrylate: 5-46 weight percent,
2. multifunctional, high-molecular acrylic resin: 2.5-20 weight percent,
3. multifunctional reactive dilution agent: 5-15 weight percent,
4. Bis-GMA and/or ethoxylated derivatives: 1-15 weight percent,
5. filler material: 2-15 weight percent,
6. organic filler material on PMMA/copolymer basis: 5-30 weight percent,
7. splinter polymerizate: 0-30 weight percent,
8. inorganic glass: 0-10 weight percent,
9. photoinitiator 0.1-2 weight percent, and
10. color pigment: 0-1 weight percent.

The compounds set forth under 1. to 10. are specifically:

1

Aliphatic urethane acrylate/-methacrylate, relative molar mass 400-700 g/mol, viscosity at 23° C.: $10^3$-$5\times10^4$ mPas.

2:

Polyester triurethane acrylate with a relative molar mass of 900-1500 g/mol, viscosity at 60° C.: $10^3$-$3\times10^4$ mPas.

3:

Generally multifunctional, aliphatic methacrylate/acrylate, glycol dimethacrylate, for example, triethylene glycol dimethacrylate, dimethacrylates containing alkyl chains such as dodecan diol dimethacrylate, polyether polyol acrylates, for example, pentaerythritol tetraacrylate.

4:

Bis-GMA or ethoxylated Bis-GMA derivatives.

5:

Pyrogenic $SiO_2$, surface according to BET 50-250 $m^2$/g, primary particle size 7-40 nm, compacted bulk density 50-150 g/l; can be advantageously hydrophobized or functionalized with silanes, preferably with methacryl silanes.

6:

Advantageously, primary particle sizes of <20 µm, delivered spray-dried in agglomerated form.

Core-shell Products:

Cross-linked PMMA core with parts of the components referred under 1 and/or 3; PMMA shell with parts of alkyl methacrylates, for example, butyl methacrylate.

Emulsion Polymerizates:

PMMA with parts of alkyl methacrylate, for example, isobutyl methacrylate (cross-linked with parts of multifunctional methacrylates/acrylates, for example, aliphatic dimethacrylates or glycol dimethacrylates).

7:

Splinter Polymerizates

Composition: aliphatic dimethacrylate, for example, dodecan diol dimethacrylate, pyrogenic $SiO_2$, as described under item 5. This mixture is polymerized, ground, and silanized and can then be used as filler material; primary particle size 15-40 µm. The preferred part of splinter polymerizate is 5-30 weight percent.

8:

Inorganic Glasses

Barium-aluminum-boron silicates $\leq$5 µm, preferably $\leq$1 µm, preferably surface-modified, for example, with silanes containing methacryl groups.

9:

Possible, Usable Photoinitiator Systems

Champerchinon, acryl phophine oxide/bisacyl phophine oxide derivatives such as hydroxy alkyl phenones, each, advantageously in combination with a synergist containing amine, for example, alkyl amino benzoate.

10:

Combination of organic color pigments and dye as well as inorganic opacifying agents.

Opacifying agent: titanium oxide

Red pigments: organic perylene pigments

Blue: anthraquinone dye

Suitable for use as inorganic filler materials are only copolymers in the form of bead polymerizates with cross-linker parts of >5 weight percent; otherwise there will be an extreme increase in viscosity over time, due to undesired swelling events. Particularly suitable in the present context are so-called core-shell polymers, consisting of a more intensely cross-linked core and a less intensely or not-cross-linked shell. This allows for defined swelling. Particularly suitable are also emulsion polymers with defined areas showing a higher degree of cross-linking, which also only swell to a limited degree locally. Due to this partial swelling, the filler materials are incorporated into the monomer matrix in such a manner that very high impact resistance values of up to approx. 8 $kJ/m^2$ can be obtained. (Product examples are bead polymerizates, for example, of the plexigum product line by the Röhm company, Darmstadt, [Germany]) which have proven themselves as suitable in the tests.)

The grain sizes of suitable polymers are advantageously in the range of $\leq$50 µm, especially $\leq$20 µm.

As an alternative, it is possible to use silicone-modified polymers, also on the basis of core-shell products.

The splinter polymer that is to be used consists of a prepolymerized mixture of multifunctional methacrylates or acrylates with parts of inorganic filler material. Used as monomers are multifunctional methacrylates/acrylates, and used as filler materials are pyrogenic silicon dioxides. The polymerized and ground mixtures are silanized for their use as filler materials, i.e. they are coated with a functional layer that contains methacrylate. This way, it is possible to achieve a chemical bond between the splinter polymerizate and the monomer matrix of the base plate material.

The grain sizes of the splinter polymerizates that are to be used are generally $\leq$30 µm; and achieving, in particular, a transparency that is as high as possible is an important criterion. The transparency of the filler material in layer thicknesses of 3 mm should be at least at 30-40%.

Optimal for use are inorganic glasses that are normally employed as central filler materials for composite materials. Quantities of under 10 weight percent are preferable, because while these inorganic filler materials improve the mechanic properties, at the same time, hey also have a negative impact on parameters such as brittleness, working properties, and plaque affinity.

Suitable for use are, for example, barium glasses and barium-aluminum-boron silicates, with grain sizes of $\leq$5 µm, especially $\leq$1 µm.

The advantages of the process according to the invention and of the prosthesis plastic according to the invention are obvious:

It is evident, first of all, that the wax index is already done on the later prosthesis base, which means that the precision of the fit, when the prosthesis is tried on by the patient, corresponds to the fit of the later prosthesis.

Furthermore, the exchange of the base plate for the wax is eliminated, resulting in higher accuracy coupled with noticeable time savings.

An after-the-fact lining step, which is necessary in practice, is often eliminated before the creation of the wax index.

The polymerization shrinkage of the entire prosthesis is reduced via the multi-step production.

Moreover, at least with the second variant of the process according to the invention, it is possible to carry out the work step by step; and the piece by piece polymerization prevents any material flow-off.

Because the work lays open during the production, a direct control of the results of any corresponding work step is possible.

Also, due to the swelling capacity and/or the possibility of chemical bonding of the filler materials, a homogeneous material with high firmness is achieved.

The adjusted viscosity of the paste remains constant over a long period of time due to the defined swelling capacity of the splinter polymerizate.

The large parts of organic filler material ensure, for example, in reference to the optical properties, a high compatibility vis-a-vis the matrix. This way, it is possible to achieve the hardening depths that are necessary for use as prosthesis material.

Due to the only small amount of parts of inorganic filler materials, the prefabricated plates are still stable in terms of their dimensions during storage, but they do not yet show the disadvantages with respect to plaque affinity and bad polishing properties of conventional composites.

Consequently, the advantages of using the prosthesis material according to the invention for partial prosthesis repair and orthodontic work is evident.

The invention will be explained in more detail in reference to the following example:

| Allocation: | Composition: Component | Mixture 1 | Mixture 2 | Mixture 3 |
|---|---|---|---|---|
| 1. | Urethane dimethacrylate | 45 | 40 | 38.5 |
| 2. | Polyester urethane triacrylate | 5.2 | 5 | 4.5 |
| 3. | Oligo ether tetraacrylate | 6.2 | 6 | 5 |
| 3. | Trimethylol propane trimethacrylate | 7.8 | 7.5 | 7 |
| 4. | Ethoxylated BIS-GMA | 3.2 | 3 | 2.8 |
| 5. | Pyrogenic SiO2 | 11.1 | 14.5 | 12 |
| 9. | Photoinitiators/stabilizers | 0.5 | 0.5 | 0.5 |
| 10. | Color pigments | 0.006 | 0.006 | 0.006 |
| 6. | Cross-linked bead polymerizate | 21 | 17.5 | 14.7 |
| 7. | Splinter polymerizate | — | 6 | 10 |
| 8. | Inorganic ultra-fine glass | — | — | 5 |
| | Mechanical Strength | | | |
| | Flexural strength Init. EN ISO 1567 > 60 MPa | 70 | 87 | 76 |
| | E-module Init. EN ISO 1567 > 2000 MPa | 2100 | 2700 | 2500 |

We claim:

1. A prosthesis material comprised of
   1. multifunctional urethane methacrylate/-acrylate: 5-46 weight percent,
   2. multifunctional, high-molecular acrylic resin: 2.5-20 weight percent,
   3. multifunctional reactive dilution agent: 5-15 weight percent,
   4. bisphenol A-glycidylmethacrylate (Bis-GMA) and/or ethoxylated derivatives: 1 -15 weight percent,
   5. filler material: 2-15 weight percent,
   6. organic filler material on polymethylmethacrylate (PMMA)/copolymer basis: 5-30 weight percent,
   7. splinter polymerizate: 5-30 weight percent,
   8. inorganic glass: 0-10 weight percent,
   9. photoinitiator: 0.1-2 weight percent, and
   10. color pigment: 0-1 weight percent.

* * * * *

UNITED STATES PATENT AND TRADEMARK OFFICE
CERTIFICATE OF CORRECTION

PATENT NO. : 7,361,697 B2  Page 1 of 1
APPLICATION NO. : 11/046933
DATED : April 22, 2008
INVENTOR(S) : Stange et al.

It is certified that error appears in the above-identified patent and that said Letters Patent is hereby corrected as shown below:

Column 3, line 25, "$\leqq 5\mu m$ preferably $\leqq 1$" should read -- $\leq 5\mu m$ preferably $\leq 1$ --

Column 3, line 59, "$\leqq 50\mu m$, especially $\leqq 20\mu m$" should read -- $\leq 50\mu m$, especially $\leq 20\mu m$ --

Column 4, line 7, "$\leqq 30\mu m$" should read -- $\leq 30\mu m$ --

Column 4, line 20, "$\leqq 5$" should read -- $\leq 5$ --

Column 4, line 21, "$\leqq 1\mu m$" should read -- $\leq 1\mu m$ --

Signed and Sealed this

Twenty-ninth Day of June, 2010

David J. Kappos
*Director of the United States Patent and Trademark Office*